(12) United States Patent
Juergens et al.

(10) Patent No.: US 10,143,831 B2
(45) Date of Patent: Dec. 4, 2018

(54) ELECTROSURGICAL SYSTEMS AND METHODS

(71) Applicant: Cynosure, Inc., Westford, MA (US)

(72) Inventors: Albert M. Juergens, Boylston, MA (US); Frank D'Amelio, Los Olivos, CA (US)

(73) Assignee: Cynosure, Inc., Westford, MA (US)

( * ) Notice: Subject to any disclaimer, the term of this patent is extended or adjusted under 35 U.S.C. 154(b) by 549 days.

(21) Appl. No.: 14/213,992

(22) Filed: Mar. 14, 2014

(65) Prior Publication Data

US 2014/0276801 A1    Sep. 18, 2014

Related U.S. Application Data

(60) Provisional application No. 61/784,627, filed on Mar. 14, 2013.

(51) Int. Cl.
*A61B 18/14*    (2006.01)
*A61N 1/04*    (2006.01)
*A61B 18/00*    (2006.01)

(52) U.S. Cl.
CPC ............ *A61N 1/04* (2013.01); *A61B 18/1402* (2013.01); *A61B 2018/0091* (2013.01); *A61B 2018/00196* (2013.01); *A61B 2018/00452* (2013.01); *A61B 2018/00922* (2013.01); *A61B 2018/00946* (2013.01); *A61B 2018/1417* (2013.01)

(58) Field of Classification Search
CPC .. A61N 1/04; A61B 18/1402; A61B 18/1482; A61B 18/1485; A61B 18/1477; A61B 2018/00916; A61B 2018/0047; A61B 2018/1417; A61B 2018/1475
See application file for complete search history.

(56) References Cited

U.S. PATENT DOCUMENTS 236,203 A    1/1881    Campbell
1,881,250 A    10/1932    Tomlinson
(Continued)

FOREIGN PATENT DOCUMENTS

CN    1697631 A    11/2005
CN    101610736 A    12/2009
(Continued)

OTHER PUBLICATIONS

Zelickson, Brian D.,et al., "Histological and Ultrastrcutrual Evaluation of the Effects fo Radiofrequency-Based Nonablative Dermal Remodeling Device," Arch Dermatol, Aug. 14, 2003, pp. 204-209, vol. 140, American Medical Association, United States.
(Continued)

*Primary Examiner* — Michael Peffley
(74) *Attorney, Agent, or Firm* — Ganz Pollard, LLC (57) ABSTRACT

An electrosurgical device can have a housing and an electrode defining an energizable surface at least partially positioned externally of the housing. The electrode can move longitudinally relative to the housing. A shank of the electrode can be positioned within the housing and configured to urge against an energizable element in the housing. The energizable element can have a longitudinally movable electrical coupler configured to electrically couple with the shank portion when the shank portion urges against the energizable element. Related methods are also disclosed.

6 Claims, 5 Drawing Sheets

(56) References Cited

U.S. PATENT DOCUMENTS

| | | | |
|---|---|---|---|
| 1,916,722 | A | 7/1933 | Ende |
| 1,943,543 | A | 1/1934 | McFadden |
| 1,945,327 | A | 1/1934 | Morse |
| 2,102,270 | A | 12/1937 | Hyams |
| 2,888,928 | A | 6/1959 | Seiger |
| 3,532,095 | A * | 10/1970 | Miller ............... A61B 18/1402 606/45 |
| 3,730,188 | A | 5/1973 | Ellman |
| 3,799,168 | A * | 3/1974 | Peters ............... A61B 18/1402 403/3 |
| 3,825,004 | A | 7/1974 | Durden, III |
| 3,858,586 | A | 1/1975 | Lessen |
| 3,879,947 | A | 4/1975 | Gaiser |
| 3,920,022 | A | 11/1975 | Pastor |
| D246,053 | S | 10/1977 | Staub et al. |
| 4,071,028 | A | 1/1978 | Perkins |
| 4,103,688 | A | 8/1978 | Edwards |
| 4,148,321 | A | 4/1979 | Wyss |
| 4,221,222 | A | 9/1980 | Detsch |
| 4,246,902 | A | 1/1981 | Martinez |
| 4,289,132 | A | 9/1981 | Rieman |
| 4,314,560 | A | 2/1982 | Helfgott |
| 4,463,759 | A | 8/1984 | Garito |
| 4,476,862 | A | 10/1984 | Pao |
| 4,492,231 | A | 1/1985 | Auth |
| 4,517,975 | A | 5/1985 | Garito |
| D281,721 | S | 12/1985 | Scanlan |
| 4,565,200 | A | 1/1986 | Cosman |
| 4,658,819 | A | 4/1987 | Harris et al. |
| 4,688,569 | A | 8/1987 | Rabinowitz |
| 4,701,193 | A | 10/1987 | Robertson et al. |
| 4,711,239 | A | 12/1987 | Sorochenko et al. |
| 4,716,897 | A | 1/1988 | Noguchi et al. |
| 4,754,754 | A | 7/1988 | Garito |
| 4,821,717 | A | 4/1989 | Wehrli |
| 4,962,766 | A | 10/1990 | Herzon |
| 4,986,839 | A | 1/1991 | Wertz et al. |
| 5,035,695 | A | 7/1991 | Weber |
| D320,271 | S | 9/1991 | Jones |
| D320,856 | S | 10/1991 | Scheller |
| 5,078,716 | A | 1/1992 | Doll |
| 5,098,430 | A | 3/1992 | Fleenor |
| 5,125,058 | A | 6/1992 | Tenerz et al. |
| 5,195,959 | A | 3/1993 | Smith |
| 5,196,007 | A | 3/1993 | Ellman |
| 5,217,458 | A | 6/1993 | Parins |
| 5,217,460 | A | 6/1993 | Knoepfler |
| 5,261,905 | A | 6/1993 | Doresey |
| 5,224,947 | A | 7/1993 | Cooper |
| 5,226,939 | A | 7/1993 | Nicolas et al. |
| 5,246,440 | A | 9/1993 | Van Noord |
| 5,267,998 | A | 12/1993 | Hagen |
| 5,281,218 | A | 1/1994 | Imran |
| 5,304,183 | A | 4/1994 | Gourlay et al. |
| D346,866 | S | 5/1994 | Lotuaco |
| 5,336,218 | A | 8/1994 | Linhares |
| 5,342,356 | A | 8/1994 | Ellman |
| D351,227 | S | 10/1994 | Patton et al. |
| D352,350 | S | 11/1994 | Rambo et al. |
| 5,360,428 | A | 11/1994 | Hutchinson |
| 5,368,560 | A | 11/1994 | Rambo et al. |
| 5,383,923 | A | 1/1995 | Webster, Jr. |
| 5,396,893 | A | 3/1995 | Oberg |
| 5,413,574 | A | 5/1995 | Fugo |
| 5,423,779 | A | 6/1995 | Yeh |
| 5,423,812 | A | 6/1995 | Ellman |
| 5,456,683 | A | 10/1995 | Fritzsch et al. |
| 5,465,248 | A | 11/1995 | Fuji |
| 5,478,303 | A | 12/1995 | Foley-Nolan |
| 5,505,728 | A | 4/1996 | Ellman |
| 5,514,131 | A | 5/1996 | Edwards |
| 5,562,503 | A | 10/1996 | Ellman |
| 5,571,101 | A | 11/1996 | Ellman |
| D376,423 | S | 12/1996 | Monea |
| 5,620,441 | A | 4/1997 | Greff et al. |
| D382,342 | S | 8/1997 | Rosen |
| 5,662,680 | A | 9/1997 | Desai |
| 5,679,401 | A | 10/1997 | Bawden |
| 5,683,387 | A | 11/1997 | Garito |
| D388,170 | S | 12/1997 | Sjostrom |
| D393,067 | S | 3/1998 | Geary et al. |
| 5,733,282 | A | 3/1998 | Ellman et al. |
| D393,715 | S | 4/1998 | Strickland |
| 5,741,250 | A | 4/1998 | Garito |
| 5,746,746 | A | 5/1998 | Garito |
| 5,755,716 | A | 5/1998 | Garito |
| 5,807,392 | A | 9/1998 | Eggers |
| 5,833,689 | A | 11/1998 | Long |
| D402,030 | S | 12/1998 | Roberts et al. |
| 5,871,524 | A | 2/1999 | Knowlton |
| 5,891,142 | A | 4/1999 | Eggers et al. |
| 5,924,206 | A | 7/1999 | Cote et al. |
| 5,948,009 | A | 9/1999 | Tu |
| 5,954,686 | A | 9/1999 | Garito |
| 5,984,918 | A | 11/1999 | Garito |
| 5,997,533 | A * | 12/1999 | Kuhns ............... A61B 18/14 606/41 |
| 5,997,733 | A | 12/1999 | Wilbur et al. |
| 6,001,077 | A | 12/1999 | Ellman |
| 6,006,755 | A | 12/1999 | Edwards |
| D422,024 | S | 3/2000 | Andrews et al. |
| 6,044,846 | A | 4/2000 | Edwards |
| 6,059,734 | A | 5/2000 | Yoon |
| 6,063,085 | A | 5/2000 | Tay et al. |
| D428,146 | S | 7/2000 | Svanberg et al. |
| 6,093,186 | A | 7/2000 | Goble |
| 6,203,762 | B1 | 3/2001 | Skalla et al. |
| 6,206,842 | B1 | 3/2001 | Tu |
| D441,077 | S | 4/2001 | Garito et al. |
| 6,228,078 | B1 | 5/2001 | Eggers et al. |
| 6,231,571 | B1 | 5/2001 | Ellman |
| 6,235,027 | B1 | 5/2001 | Herzon |
| 6,238,388 | B1 | 5/2001 | Ellman |
| 6,238,394 | B1 | 5/2001 | Garito |
| D453,222 | S | 1/2002 | Garito |
| 6,387,093 | B1 | 5/2002 | Ellman |
| 6,402,742 | B1 | 6/2002 | Blewet et al. |
| 6,409,726 | B1 | 7/2002 | Ellman |
| 6,417,532 | B2 | 7/2002 | Tsunoda et al. |
| 6,432,105 | B1 | 8/2002 | Ellman |
| 6,530,924 | B1 | 3/2003 | Ellman |
| 6,544,210 | B1 | 4/2003 | Trudel et al. |
| 6,562,032 | B1 | 5/2003 | Ellman |
| 6,562,036 | B1 | 5/2003 | Ellman |
| 6,572,613 | B1 | 6/2003 | Ellman et al. |
| 6,585,791 | B1 | 7/2003 | Garito et al. |
| 6,605,080 | B1 | 8/2003 | Altshuler et al. |
| 6,652,514 | B2 | 11/2003 | Ellman |
| 6,663,620 | B2 | 12/2003 | Altshuler et al. |
| 6,679,881 | B1 | 1/2004 | Bybee |
| 6,749,608 | B2 | 6/2004 | Garito |
| 6,749,624 | B2 | 6/2004 | Knowlton |
| D494,270 | S | 8/2004 | Reschke |
| 6,802,842 | B2 | 10/2004 | Ellman |
| 6,926,717 | B1 | 8/2005 | Garito |
| 6,974,451 | B2 | 12/2005 | Altshuler et al. |
| 6,976,985 | B2 | 12/2005 | Altshuler et al. |
| 6,994,707 | B2 | 2/2006 | Ellman |
| 7,070,604 | B1 | 7/2006 | Garito |
| 7,090,649 | B2 | 8/2006 | Kang |
| 7,094,231 | B1 | 8/2006 | Ellman |
| 7,147,634 | B2 | 12/2006 | Nesbitt |
| 7,160,295 | B1 | 1/2007 | Garito |
| D538,936 | S | 3/2007 | Bohmel et al. |
| 7,258,689 | B2 | 8/2007 | Tutino |
| 7,276,058 | B2 | 10/2007 | Altshuler et al. |
| D555,803 | S | 11/2007 | Garito |
| 7,351,252 | B2 | 4/2008 | Altshuler et al. |
| 7,427,289 | B2 | 9/2008 | Sierra et al. |
| 7,479,140 | B2 | 1/2009 | Ellman |
| 7,507,232 | B1 | 3/2009 | Garito |
| 7,763,016 | B2 | 7/2010 | Altshuler et al. |
| D625,412 | S | 10/2010 | Garito |
| 7,875,026 | B1 | 1/2011 | Garito |

(56) References Cited

U.S. PATENT DOCUMENTS

| | | | |
|---|---|---|---|
| 7,935,110 B1 | 5/2011 | Garito | |
| 7,947,037 B1 | 5/2011 | Garito | |
| 7,975,702 B2 | 7/2011 | Cho et al. | |
| 8,002,768 B1 | 8/2011 | Altshuler et al. | |
| 8,113,209 B2 | 2/2012 | Masotti et al. | |
| 8,172,835 B2 | 5/2012 | Leyh et al. | |
| 8,190,243 B2 | 5/2012 | Welches et al. | |
| 8,317,782 B1 | 11/2012 | Ellman et al. | |
| 8,321,031 B1* | 11/2012 | Ellman | A61B 18/14 607/100 |
| 8,359,104 B2 | 1/2013 | Epstein | |
| 8,454,591 B2 | 6/2013 | Leyh et al. | |
| 8,540,705 B2 | 9/2013 | Mehta | |
| 8,608,737 B2 | 12/2013 | Mehta et al. | |
| 8,663,216 B2 | 3/2014 | Davison et al. | |
| 8,845,630 B2 | 9/2014 | Mehta et al. | |
| 8,915,948 B2 | 12/2014 | Altshuler et al. | |
| 8,961,511 B2 | 2/2015 | Parmer | |
| 8,998,891 B2 | 4/2015 | Garito | |
| 9,271,785 B2 | 3/2016 | Parmer et al. | |
| 9,345,531 B2 | 5/2016 | Furnish | |
| 9,415,235 B2 | 8/2016 | Galen et al. | |
| 2001/0018606 A1 | 8/2001 | Ingle et al. | |
| 2002/0032439 A1 | 3/2002 | Hareyama | |
| 2002/0077626 A1 | 6/2002 | Ellman | |
| 2002/0188284 A1 | 12/2002 | To | |
| 2003/0050634 A1 | 3/2003 | Ellman | |
| 2003/0130711 A1 | 7/2003 | Pearson | |
| 2003/0139753 A1 | 7/2003 | Wang | |
| 2003/0159700 A1 | 8/2003 | Laufer | |
| 2003/0216727 A1 | 11/2003 | Long | |
| 2003/0216728 A1 | 11/2003 | Stern et al. | |
| 2003/0236487 A1 | 12/2003 | Knowlton | |
| 2004/0002705 A1 | 1/2004 | Knowlton | |
| 2004/0030329 A1 | 2/2004 | Hagg | |
| 2004/0049251 A1 | 3/2004 | Knowlton | |
| 2004/0064175 A1 | 4/2004 | Lessar | |
| 2004/0111087 A1 | 6/2004 | Stern | |
| 2004/0116979 A1 | 6/2004 | Truckai et al. | |
| 2004/0167516 A1 | 8/2004 | Cucin | |
| 2004/0181213 A1 | 9/2004 | Gondo | |
| 2004/0186535 A1 | 9/2004 | Knowlton | |
| 2004/0210214 A1 | 10/2004 | Knowlton | |
| 2004/0236203 A1 | 11/2004 | Francesco | |
| 2005/0004564 A1 | 1/2005 | Wham et al. | |
| 2005/0090816 A1 | 4/2005 | McClurken et al. | |
| 2005/0137662 A1 | 6/2005 | Morris et al. | |
| 2005/0154385 A1 | 7/2005 | Heim | |
| 2005/0256524 A1 | 11/2005 | Long | |
| 2006/0009757 A1 | 1/2006 | Long | |
| 2006/0052847 A1 | 3/2006 | Davenport et al. | |
| 2006/0173518 A1 | 8/2006 | Kreindel | |
| 2006/0259102 A1 | 11/2006 | Slatkine | |
| 2007/0005053 A1 | 1/2007 | Dando | |
| 2007/0233191 A1 | 2/2007 | Parmer | |
| 2007/0055226 A1 | 3/2007 | Garito | |
| 2007/0106349 A1 | 5/2007 | Karni | |
| 2007/0213792 A1 | 9/2007 | Yaroslavsky et al. | |
| 2007/0282318 A1 | 12/2007 | Spooner | |
| 2008/0004678 A1 | 1/2008 | Kreindel | |
| 2008/0091184 A1 | 4/2008 | Knopp et al. | |
| 2008/0091185 A1 | 4/2008 | Mcgill et al. | |
| 2008/0125775 A1 | 5/2008 | Morris | |
| 2008/0183251 A1 | 7/2008 | Zion | |
| 2008/0262490 A1 | 10/2008 | Williams | |
| 2009/0012511 A1 | 1/2009 | Welches et al. | |
| 2009/0018531 A1 | 1/2009 | Welches et al. | |
| 2009/0054956 A1 | 2/2009 | Sierra et al. | |
| 2009/0062786 A1 | 3/2009 | Garito | |
| 2009/0093864 A1 | 4/2009 | Anderson | |
| 2009/0138011 A1 | 5/2009 | Epstein | |
| 2009/0248004 A1 | 10/2009 | Altshuler et al. | |
| 2009/0306647 A1 | 12/2009 | Leyh | |
| 2009/0306648 A1 | 12/2009 | Podhajsky et al. | |
| 2010/0023008 A1 | 1/2010 | Heard | |
| 2010/0030212 A1 | 2/2010 | Aramayo | |
| 2010/0114088 A1 | 5/2010 | Buchman | |
| 2010/0211060 A1 | 8/2010 | Baron et al. | |
| 2010/0217254 A1 | 8/2010 | Mehta | |
| 2010/0228243 A1 | 9/2010 | Mehta | |
| 2010/0249772 A1 | 9/2010 | Mehta et al. | |
| 2010/0262135 A1 | 10/2010 | Berube | |
| 2010/0312233 A1* | 12/2010 | Furnish | A61B 18/14 606/33 |
| 2011/0046523 A1 | 2/2011 | Altshuler et al. | |
| 2011/0144729 A1 | 6/2011 | Weber | |
| 2011/0178584 A1 | 7/2011 | Parmer | |
| 2012/0022512 A1 | 1/2012 | Vaynberg | |
| 2012/0265193 A1 | 10/2012 | Lischinsky | |
| 2013/0245728 A1 | 9/2013 | Galen et al. | |
| 2013/0296835 A1 | 11/2013 | Sierra et al. | |
| 2014/0025033 A1 | 1/2014 | Mirkov et al. | |
| 2014/0182335 A1 | 7/2014 | Lee et al. | |
| 2014/0276768 A1 | 9/2014 | Juergens | |
| 2015/0005759 A1 | 1/2015 | Welches et al. | |
| 2015/0094914 A1 | 4/2015 | Abreu | |
| 2015/0297908 A1 | 10/2015 | Alinsod et al. | |
| 2015/0327926 A1 | 11/2015 | Parmer | |
| 2016/0135876 A1 | 5/2016 | Parmer et al. | |
| 2016/0263387 A1 | 9/2016 | Alinsod et al. | |
| 2016/0263388 A1 | 9/2016 | Alinsod et al. | |
| 2016/0263389 A1 | 9/2016 | Alinsod et al. | |
| 2016/0296278 A1 | 10/2016 | Galen et al. | |
| 2017/0071651 A1 | 3/2017 | Allan et al. | |
| 2017/0182334 A1 | 6/2017 | Altshuler et al. | |
| 2017/0333249 A1 | 11/2017 | Herchman, Jr. et al. | |
| 2018/0001103 A9 | 1/2018 | Alinsod et al. | |

FOREIGN PATENT DOCUMENTS

| | | |
|---|---|---|
| CN | 101905059 A | 12/2010 |
| DE | 2011035 A1 | 10/1970 |
| DE | 3627221 | 2/1988 |
| DE | 9102778 U1 | 5/1991 |
| DE | DE4423216 A1 | 8/1995 |
| DE | 19850663 A1 | 3/2001 |
| DE | 10138235 A | 1/2003 |
| EP | 0368532 A2 | 5/1990 |
| EP | 0423757 A1 | 4/1991 |
| EP | 0480639 A2 | 4/1992 |
| EP | 0332308 A2 | 9/1998 |
| EP | 1707147 A1 | 10/2006 |
| EP | 2258296 A1 | 12/2010 |
| EP | 2967711 A2 | 1/2016 |
| GB | 2154881 A | 9/1985 |
| GB | 2490788 A | 11/2012 |
| JP | S63317073 A | 12/1988 |
| JP | H0795985 A | 4/1995 |
| JP | H08168495 A | 7/1996 |
| WO | WO1996022742 A1 | 8/1996 |
| WO | WO1996039088 A1 | 12/1996 |
| WO | WO1997015238 A1 | 5/1997 |
| WO | WO1998016162 A1 | 4/1998 |
| WO | WO1998038932 A1 | 9/1998 |
| WO | WO2003103522 A1 | 12/2003 |
| WO | WO2004090939 A2 | 10/2004 |
| WO | WO2008012827 | 1/2008 |
| WO | WO2008112931 A2 | 9/2008 |
| WO | WO2009031995 A1 | 3/2009 |
| WO | WO2009053117 A2 | 4/2009 |

OTHER PUBLICATIONS

Hantash, Basil M., et al., "Bipolar Fractional Radiofrequency Treatment Induces Neoelastogenesis and Neocollagenesis," Lasers in Surgery and Medicine, Nov. 4, 2008, pp. 1-9, vol. 41, Wiley-Liss, Inc., United States.

Gonzalex-Suarez, Ana, et al., "Thermal and Elastic Response of Subcutaneous Tissue With Different Fibrous Septa Architectures to RF Heating: Numerical Study," Lasers in Surgery and Medicine, Oct. 4, 2014, pp. 183-195, vol. 47, Wiley Periodicals, Inc., United States.

(56) References Cited

OTHER PUBLICATIONS

Kist, David, et al., "Ultrastructural Evaluation of Multiple Pass Low Energy Versus Single Pass High Energy Radio-Frequency Treatment," Lasers in Surgery and Medicine, Jan. 5, 2006, pp. 150-154, vol. 38, Wiley-Liss, Inc., United States.

"The Effect of Heat on Collagen and Neocollagenesis," Ultherapy.com, Jul. 20, 2011, 78 pages, available from http://www.ultherapy.com/uploads/document/professional/Effects-of-Temperature-on-Collagen.pdf. (last accessed May 9, 2018).

Abraham, Manoj T., et al. "Monopolar Radiofrequency Skin Tightening," Facial Plastic Surgery Clinics of North America, 2007, pp. 169-177, vol. 15, Elsevier Inc.

Sadick, Neil, "Tissue Tightening Technologies: Fact or Fiction," Aesthetic Surgery Journal, Dec. 11, 2007, pp. 180-188, vol. 28 No. 2, Sage Publications, United States.

Lauback, Hans J., et al., "Intense Focused Ultrasound: Evaluation of a New Treatment Modality for Precise Microcoagulation within the Skin," American Society for Dermatologic Surgery, Inc., May 2008, pp. 727-734, vol. 34, Blackwell Publishing, United States.

White, W, Matthew, et al., "Selective Transcutaneous Delivery of Energy to Porcine Soft Tissues Using Intense Ultrasound (IUS)," Lasers in Surgery and Medicine, Dec. 27, 2007, pp. 67-75, vol. 40, Wiley-Liss, Inc., United States.

Hayashi, Kei, et al., "The Effect of Thermal Heating on the Length and Histologic Properties of the Glenohumeral Joint Capsule," The American Journal of Sports Medicine, 1997, pp. 107-112, vol. 25 No. 1, Sage Publications, United States.

Vangsness Jr., C. Thomas, et al., "Collagen Shortening: An Experimental Approach with Heat," Clinical Orthopedics and Related Research, Mar. 24, 1995, pp. 267-271, vol. 337, Lippincott-Raven Publishers.

Lin, Sung-Jan, et al., "Monitoring the Thermally Induced Structural Transitions of Collagen by Use of Second-Harmonic Generation Microscopy," Optics Letters, Mar. 15, 2005, pp. 622-624, vol. 30 No. 6, Optical Society of America.

Paul, Malcolm, et al., "Three-Dimensional Radiofrequency Tissue Tightening: A Proposed Mechanism and Applications for Body Contouring," Aesth Platic Surgery, Jul. 6, 2010, pp. 87-95, vol. 35., Springer.

Hayashi, Kel, et al., "Effect of Nonablative Laser Energy on the Joint Capsule: An in Vivo Rabbit Study Using a Holmium:YAG Laser," Lasers in Surgert and Medicine, Feb. 21, 1996, pp. 164-171, vol. 20, Wiley-Liss, Inc., United States.

Invitation to Pay Additional Fees for PCT Application No. PCT/US2017/040585, dated Oct. 13, 2017, 23 pages.

International Search Report and Written Opinion for PCT Application No. PCT/US2017/040585, dated Dec. 6, 2017, 24 pages.

Third Party Submission in PCT Application No. PCT/US2017/040585, filed Jan. 29, 2018, 30 pages.

Third Party Submission in U.S. Appl. No. 15/640,710, filed Feb. 7, 2018, 58 pages.

Fitzpatrick, et al. (2003). 'Multicenter study of noninvasive radiofrequency for periorbital tissue tightening'. Lasers in Surgery and Medicine 2003; 33:232-242. (12 page total).

Fritz, et al. (2004). 'Radiofrequency treatment for middle and lower face laxity'. Arch Facial Plastic Surgery 2004; 6:370-373. (4 pages total).

Kushikata, et al., (2005). 'Is topical anesthesia useful in noninvasive skin tightening using radiofrequency' J. Dermatologic Surgery 2005; 31:526-533. (8 page total).

Brunelle et al, A Bipolar Electrode for Vascular Electrocoagulation with Alternating Current. Radiology, vol. 137, No. 1, pp. 239 240, Oct. 1980.

Extended European Search Report dated Nov. 8, 2016 in European Patent Application No. 14768330.4.

\* cited by examiner

ELECTROSURGICAL SYSTEMS AND METHODS

RELATED APPLICATIONS

This application claims the benefit of and priority to U.S. Provisional Application Ser. No. 61/784,627, filed Mar. 14, 2013, the contents of which are hereby incorporated by reference as if recited in full herein for all purposes.

BACKGROUND

The innovations and related subject matter disclosed herein (collectively referred to as the "disclosure") generally pertain to electrosurgical systems, such as electrosurgical devices and related electrical circuitry and methods. More particularly, but not exclusively, the innovations relate to electrosurgical systems having a movable electrode configured to accommodate a variation in spacing between a handpiece held by an operator (e.g., in an operator's hand) and an intended treatment site (e.g., in contact with a portion of the movable electrode). For example, an electrosurgical handpiece can have a housing configured to be grasped by a user and an energizable electrode configured to move relative to the housing. With such a handpiece, the electrode can continuously provide a therapeutic energy to a treatment site notwithstanding that an operator's hand (and the handpiece) might move relatively closer to and relatively farther from the treatment site during the course of therapy. In some particular embodiments of disclosed electrosurgical systems, a movable electrode can also be configured to reduce or eliminate arcing between an energizable surface of the electrode and a patient's skin.

Figure 1:
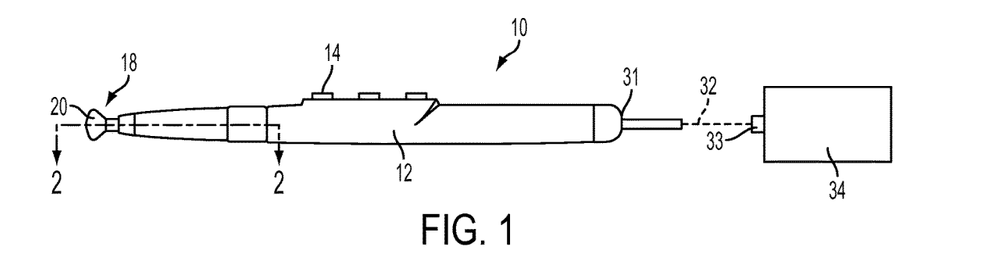
FIG. 1 illustrates an example of an electrosurgical system including an electrosurgical device.

U.S. patent application Ser. No. 13/175,618, published as U.S. Publication No. 2013/0006239, (referred to as "the '618 Application" and the contents of which are incorporated herein in their entirety, for all purposes) is commonly owned with this application and discloses, inter alia, an electrosurgical system of the type shown in FIG. 1, herein. FIG. 1 shows an electrosurgical system having a control unit 34 and an electrosurgical device 10. The electrosurgical device 10 includes a housing 12, e.g., for containing circuitry, and an energizable electrode 18 configured to treat a target site on or in a patient's body. The housing 12 can be configured as a handpiece, as shown for example in FIG. 1. In other instances, a graspable handpiece is spaced from the housing.

The control unit 34 is configured to provide power to the electrosurgical device 10 for energizing the electrode. As described more fully in the '618 Application, the control unit 34 can be configured to provide energy having a selected combination of waveform and frequency. Some control units 34 are configured to provide RF energy to the electrosurgical device 10.

As FIG. 1 shows, a cable 32 can extend between an electrical connector 33 on the control unit 34 and an electrical connector 31 on the electrosurgical device so as to electrically couple one or more conductive elements on or within the device 10 to one or more corresponding conductive elements of the controller 34. Some known control units provide three output terminals, with one of the terminals being an energizable terminal for conveying therapeutic energy, e.g., RF energy, to an energizable element of a handpiece. Such a control unit 34 is usually configured to energize the energizable terminal when a circuit between the two remaining output terminals is completed, as through the closing of a user actuatable switch 14.

Some known electrosurgical control units, such as control units manufactured by Ellman International, Inc. under the brand SURIGTRON and described in U.S. Pat. No. 6,652,514, the contents of which are incorporated herein by reference in their entirety, provide a three-wire output connector for powering and controlling electrosurgical handpieces. Conventional control units can generate, for example, one or more radio-frequency (RF) modulated waveforms, e.g., at a frequency of about 4 mega-Hertz (MHz), which can be delivered to a target site by way of an electrosurgical handpiece having an energizable electrode defining an active surface.

In some cases, the active surface of an electrosurgical system can be configured for non-ablative electrosurgery. As used herein, an ablative procedure is one where the electrode and power settings result in cutting, coagulation, vaporization or other such traumatic disruption to the integrity of treated tissue, and a non-ablative procedure is one where such cutting, coagulation, vaporization or other such traumatic disruption to the integrity of treated tissue does not result.

U.S. patent application Ser. No. 12/455,661, published as U.S. Pub. No. 2010/0312233, which is also owned by the Assignee of this application, and which is hereby incorporated by reference in its entirety, describes, inter alia, shock-free electrosurgical handpieces. Some handpieces described in the '233 Publication have an internal switch that prevents an active electrode surface from being energized unless the surface is in actual contact with a patient's skin. A de-energized electrode surface reduces or eliminates the likelihood that a patient might receive an electrical shock from an electrical arc spanning an air gap between the electrode surface and the patient's skin as the electrode is applied to or removed from the patient's skin. In some handpieces described in the '233 Publication, arcing can occur inside the handpiece between a portion of the electrode and an energizable element within the handpiece if the electrode becomes spaced from the energizable element, as when a user lifts the handpiece away from a treatment site and before the electrode lifts away from the treatment site.

However, in some instances, a user can inadvertently lift the handpiece away from the treatment site while maintaining physical contact between the electrode and the treatment site. Such inadvertent lifting of the handpiece away from the treatment site can inadvertently cause the electrode to separate from the energizable element, allowing arcing between the electrode and the energizable element to occur. Over many cycles, such arcing can degrade one or more electrically conductive surfaces of the internal switch. Inadvertent opening and closing of the internal switch can prematurely degrade one or more such electrically conductive surfaces of the internal switch.

Accordingly, there remains a need for improved electrosurgical systems, including improved electrosurgical handpieces, configured to accommodate position-dependent variations in the force applied toward (or away from) a treatment site by a user. There also remains a need for such improved electrosurgical systems configured to prevent, or at least inhibit or otherwise reduce the occurrence of, inadvertent arcing within the handpiece. As well, a need remains for an improved electrosurgical handpiece configured to prevent or at least inhibit premature degradation of an internal switch or other portion of an electrical circuit associated with the handpiece.

SUMMARY

The innovations disclosed herein overcome many problems in the prior art and address one or more of the aforementioned as well as other needs. The innovations disclosed herein generally, but not exclusively, pertain to certain aspects of electrosurgical devices, for example, handpieces configured to permit a handpiece housing move relative to an energizable, electrosurgical electrode while maintaining a continuous supply of electrical energy to the electrode.

In some disclosed handpieces, a switch is positioned internally of a handpiece housing. A portion of the switch is configured to permit the housing to move relative to a corresponding energizable electrode throughout a selected range of motion while maintaining sufficient electrical continuity through the switch to maintain a continuous supply of electrical energy to the electrode. In but one of many such handpiece embodiments, the selected range of motion can correspond to a vertical range of motion defined according to an anatomy of the user's hand and wrist as the user's hand executes a circular, trochoidal or other treatment-related path during an electrosurgical therapy.

The foregoing and other features and advantages will become more apparent from the following detailed description of disclosed embodiments, which proceeds with reference to the accompanying drawings.

BRIEF DESCRIPTION OF THE DRAWINGS

Unless specified otherwise, the accompanying drawings illustrate aspects of the innovative subject matter described herein.

FIG. 2 illustrates a partial cross-sectional view of the electrosurgical device shown in FIG. 1. In FIG. 2, the device is shown in an at-rest configuration.

FIG. 3 illustrates a partial cross-sectional view of the electrosurgical device shown in FIG. 1. In FIG. 3, the device is shown in an activatable configuration.

FIG. 5 illustrates a partial cross-sectional view of the innovative electrosurgical shown in FIG. 4. In FIG. 5, the device is shown in an activatable configuration.

FIG. 6 illustrates a partial cross-sectional view of the innovative electrosurgical similar shown in FIG. 4. In FIG. 6, the device is shown in another activatable configuration.

FIG. 7 illustrates a partial cross-sectional view of an alternative innovative electrosurgical device of the type shown in FIG. 4. In FIG. 7, the device is shown in an activatable configuration, similar to the activatable configuration shown in FIG. 5.

DETAILED DESCRIPTION

The following describes various principles related to electrosurgical systems by way of reference to specific examples of electrosurgical handpieces. In some innovative embodiments, a handpiece can constitute an electrosurgical instrument configured to treat or otherwise manipulate a target site on or in a patient's body.

One or more of the principles can be incorporated in various system configurations to achieve any of a variety of system characteristics. Systems described in relation to particular applications, or uses, are merely examples of systems incorporating the innovative principles disclosed herein and are used to illustrate one or more innovative aspects of the disclosed principles. Accordingly, electrosurgical systems having attributes that are different from those specific examples discussed herein can embody one or more of the innovative principles, and/or can be used in applications not described herein in detail, for example in ablative surgical applications. Accordingly, such alternative embodiments also fall within the scope of this disclosure.

Overview

U.S. patent application Ser. No. 12/455,661 and U.S. patent application Ser. No. 13/175,618 disclosed electrosurgical handpieces similar to the one shown in FIG. 1. During use of such an electrosurgical handpiece, a medical practitioner or other operator can apply an electrosurgical therapy to a treatment site by sweeping an energizable electrode across a region of a patient's skin along a generally circular, trochoidal, or other selected path. Ergonomic considerations and anatomic limitations of the operator's hand and wrist can cause the handpiece and/or the electrode to urge toward a treatment site with a position-dependent force during an electrosurgical treatment session. For example, based on the anatomy of a user's hand and wrist and with the same degree of perceived effort, the user can urge the handpiece toward a treatment site with a relatively higher force when the user's hand and wrist is in one orientation (e.g., in flexion such that the electrode is positioned relatively proximal to the user) as compared to another orientation (e.g., in extension such that the electrode is positioned relatively distally from the user).

Some electrosurgical devices of the type disclosed herein permit the energizable electrode to move relative to the handpiece while the electrode is in an activatable configuration (e.g., a configuration in which a switch is closed to electrically couple the electrode with an energized or energizable power element within the handpiece). A switch positioned internally relative to some innovative electrosurgical devices can be configured to interrupt a supply of RF energy (or other electrical current) to the electrode before the electrode is lifted from a treatment site.

As well, some disclosed switches have a movable element configured to electrically couple with the energizable electrode. Some disclosed movable elements are configured to permit the energizable electrode to move within a selected range of motion relative to the handpiece while maintaining an electrical coupling with the movable element of the switch. A limiter can limit a range of motion of the movable element of the switch such that the energizable electrode can electrically decouple from the movable element of the switch if the energizable electrode moves beyond the selected range of motion, e.g., into a second selected range of motion.

Some electrosurgical devices disclosed herein are configured for non-ablative electrosurgery. Some disclosed electrosurgical devices are configured to prevent traumatic disruption to a tissue as well as to keep any tissue disruption below a patient's pain threshold. For example, some disclosed electrosurgical devices are configured to deliver energy to a patient's skin without the need for anesthetizing the patient. Although difficult to quantify the precise limits of such power thresholds, applying an energy flux of 4,000 Watts per square centimeter ($W/cm^2$) for about one second (1 s) probably would not ablate skin tissue, but might cause necrosis of some tissue. On the other hand, it is presently believed that an energy flux of about 2,000 $W/cm^2$ applied for between about 2 s and about 3 s can be applied to skin tissue to obtain desirable clinical outcomes. Lower flux levels can be applied for longer times, and higher flux levels might be applied for shorter times, without damaging tissues.

Internal Couplers

FIG. 1 shows a schematic view of one possible example of an electrosurgical device 10 having a housing 12, an energizable electrode 18 extending from a distal end of the device and a cable 32 extending from a connector 31 positioned adjacent a proximal end of the device. A device 10 (shown in FIG. 1) can have a housing 12 with an energizable electrode element 18 extending from a distal end of the housing. An electrical connector 31 have a selected number of electrical couplers can be positioned adjacent a proximal end of the housing. A cable 32 can extend between and electrically couple the device 10 and the control unit 34. In this embodiment, the housing 12 serves as a handpiece. In other possible embodiments, the housing 12 can be spaced from the graspable handpiece. For example, the housing could be, for example, a shaft positioned between an electrode and a handpiece.

As used herein, a "handpiece" means an instrument configured such that a user can hold it in his hand during use. Usually, a handpiece is spaced from an instrument portion (e.g., an energizable patient contact surface 20) configured to be used on or inserted into a patient's body. Hereinafter, a handpiece will be used as a representative embodiment of a housing 12.

Figure 2:
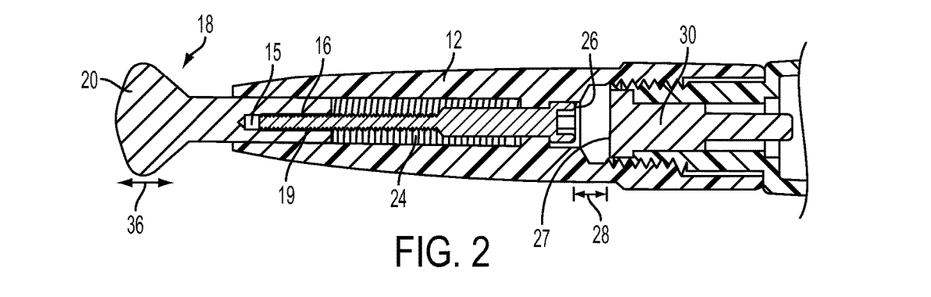
Figure 3:
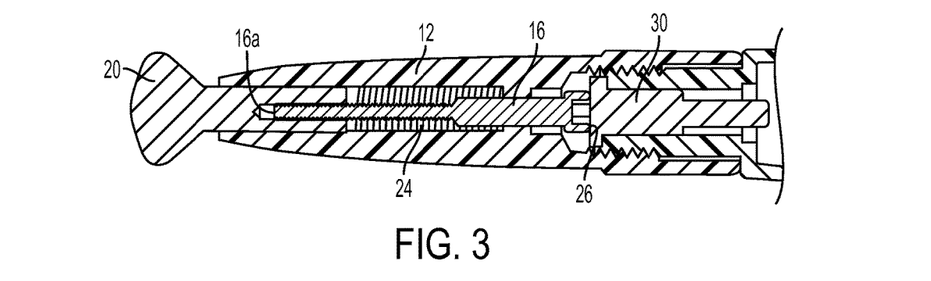

The electrode 18 can define a non-ablative contact surface 20. The electrode 18 can be longitudinally movable to open and close a gap 28 between an electrically conductive power element 30 and the electrode forming a mechanical switch within the handpiece. FIG. 2 shows the gap 28 in an open position and FIG. 3 shows the gap in a closed position. As the partial cross-sectional view in FIG. 2 shows, the energizable electrode 18 can have a longitudinally oriented and electrically conductive shank 16 extending proximally inside the housing 12. The handpiece 10 can also have a proximally positioned power element 30 that can be electrically coupled with an energizable power source (e.g., a power pin of the proximally positioned connector 31 configured to electrically couple the cable 32 to the device 10). The illustrated power element 30 is immovable relative to the housing 12.

The illustrated electrode 18 defines an internally threaded bore 19 that threadably engages a correspondingly threaded external surface of the shank 16, leaving an open region 15 between a recessed end-surface of the bore 19 and a distal end 16a of the shank 16, as shown in FIGS. 2 and 3. In other embodiments, the shank 16 and the electrode can form a unitary construction. In still other embodiments, the shank and the electrode can be (longitudinally) slidingly engaged with each other, as when the threaded bore 19 and the external surface of the shank lack matingly engageable threads. The elongated electrically-conductive shank 16 and the electrode 18 can together move longitudinally of the handle 12 between a distal position (FIG. 2) and a proximal position (e.g., FIG. 3). As shown in FIG. 2, the electrode 18 can be outwardly biased by an internally positioned compression spring 24 such that the electrode is biased toward the distal, at-rest position.

When displaced from the at-rest position shown in FIG. 2, the electrode can return to the distal position under the biasing force of the spring 24. In the at-rest, distal position, the circuit-contact surface 26 of the shank 16 and the electrode-contact surface 27 of the power element 30 are so spaced from each other as to form a gap 28 and electrically decouple the circuit-contact surface of the shank 16 from the electrode-contact surface of the power element 30 (e.g., the gap 28 is sized such that a voltage potential between the surfaces 26, 27 is insufficient to cause arcing between the surfaces).

The electrode 18 can be urged proximally, as by contact between the surface 20 of the electrode 18 and a patient's skin, toward a proximal position in which the gap 28 between the proximal end of the shank 16 and the distal end of the power element 30 is closed, as shown in FIG. 3. In such a proximal position, the circuit-contact surface 26 of the shank 16 can urge against the electrode contact surface 27 of the power element 30. Upon releasing a proximally directed longitudinal force applied to the electrode 18, the electrode can return to the at-rest position under the biasing force of the spring.

The handpiece 12 can be electrically-insulating and can have a user-operable switch 14 configured to close a control circuit configured to permit the power element 30 to be energized. When the power element 30 is energized and the gap 28 is closed, arcing can occur between the circuit-contact surface 26 and the electrode-contact surface 27 as the electrode 18 is moved in a proximal direction.

Movable Couplers

Figure 4:
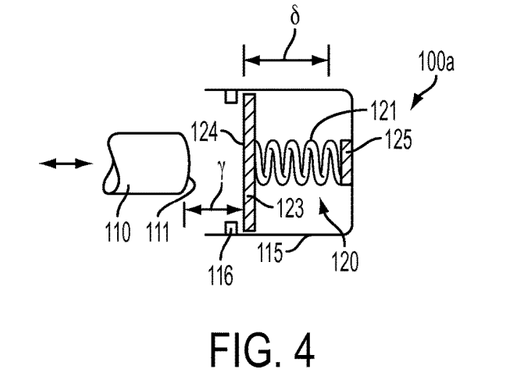
FIG. 4 illustrates a partial cross-sectional view of an innovative electrosurgical device having an energizable electrode configured to move relative to a housing during an electrosurgical therapy. The device is shown in an at-rest configuration in FIG. 4.
Figure 8:
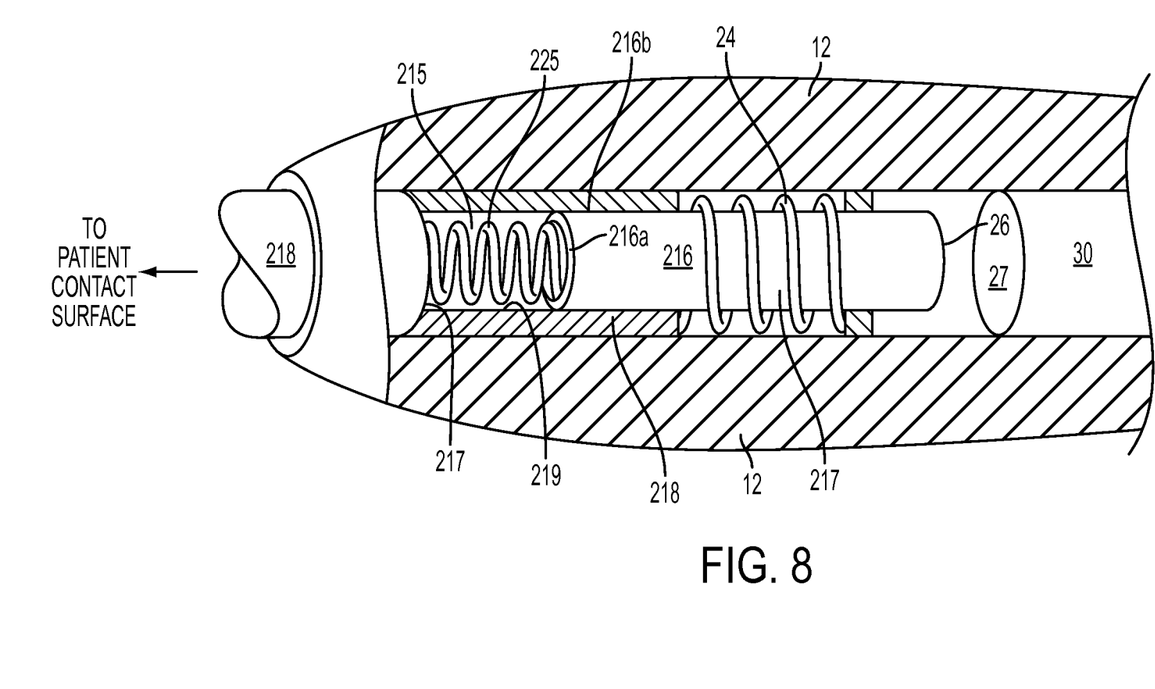
FIG. 8 illustrates an isometric, partially sectioned view of a portion of an innovative electrosurgical device, in an at-rest position, as disclosed herein.

In the embodiment of the power element 30 shown in FIGS. 2 and 3, the power element is immovable relative to the housing 12 and the shank 16 is immovable relative to the electrode 18. However, some disclosed electrosurgical devices are configured to permit an energizable electrode to move while maintaining an electrical coupling between an energized or energizable power element and the energizable electrode. For example, FIG. 4 shows a proximal end portion 110 of an electrode shank spaced apart by a distance, $\gamma$, from an energizable power element 115 having a movable element 123. As another example, FIG. 8 shows an electrode 218 slidably engaged with a movable shank 216.

In FIG. 4, the energizable power element 115 has a first electrical coupler 125 and a second electrical coupler 123. The first electrical coupler 125 can be immovable relative to the handpiece (e.g., a handpiece similar to the handpiece 10). The second electrical coupler 123 can be movable relative to the first electrical coupler. The first electrical coupler, the second electrical coupler, or both, can be formed of plated or unplated beryllium copper, or any other suitable electrically conductive alloy. As but one example, one or both electrical couplers can comprise a gold-plated beryllium copper alloy.

In some embodiments, the second electrical coupler 123 can be configured for one-degree-of-freedom motion, as with the device shown in FIG. 4. For example, the illustrated second electrode coupler 123 is configured to permit a selected degree of movement (e.g., translation) along a major (e.g., a longitudinal) axis and to permit a relatively smaller degree of movement (e.g., translation) along one or more minor axes. As but one example, the second electrode coupler 123 shown in FIG. 4 can translate along a major, longitudinal axis by a distance, $\delta$, from the at-rest configuration shown in FIG. 4. Specifically, the second electrical coupler 123 is configured to translate longitudinally of the handpiece (not shown) in correspondence with the proximal end portion 110 of the electrode shank.

In other embodiments, the second electrode coupler 123 can be configured to move laterally relative to the electrode shank. For example, the coupler 123 can have a slightly smaller transverse dimension than the housing of the energizable power element 115, permitting a selected degree of translation in a direction transverse to the electrode shank.

In still other embodiments, the second electrode coupler 123 can be configured to rotate about an axis transverse relative to or parallel with the electrode shank.

An electrically conductive element 120 can electrically couple the electrical couplers 123, 125 to each other, as in the embodiment shown in FIG. 4. The electrically conductive element 120 can comprise any suitable electrical conductor, for example, a wire having a suitable gage for a selected current-carrying capacity.

The electrical coupler 125 can be configured to receive electrical energy similarly to the electrically conductive, immovable power element 30 shown in FIGS. 2 and 3. When the electrical coupler 125 is energized, the second electrical coupler 123 can be energized by way of electrical conduction through the electrically conductive element 120.

Figure 5:
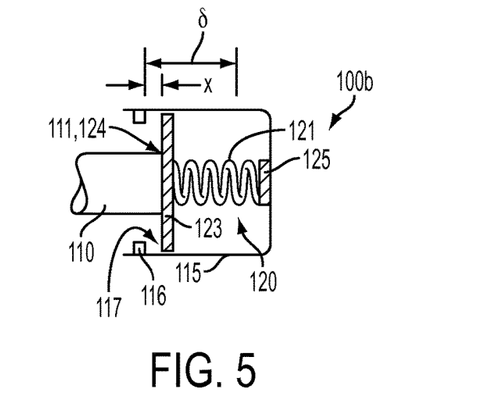
Figure 6:
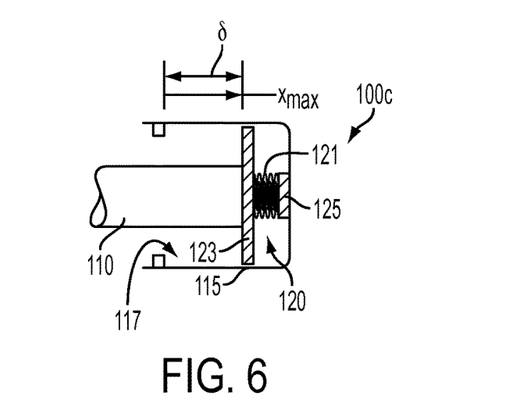
Figure 7:
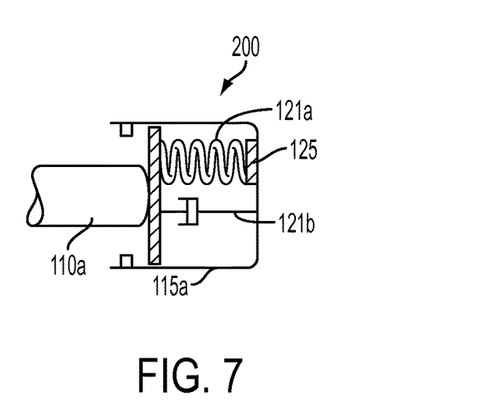

The second electrical coupler 123 can comprise an electrically conductive plate element configured to move longitudinally within the power element 115 from an at-rest configuration 100a, shown in FIG. 4, to an in-use (or activatable) configuration 100b, 100c, as indicated in FIGS. 4, 5 and 6.

In the at-rest configuration shown in FIG. 4, the gap between the end face 111 and the face portion 124 of the power element 115 is sufficiently large as to insulate the end face 111 from the face portion 124, electrically decoupling the end portion 110 of the shank from the energizable element 115. For example, the gap can be sized so as to prevent arcing through the air (or other dielectric material) between the end face 111 and the face portion 124 under a normal operating voltage potential applied across the gap.

The electrode 18 can be urged proximally within the handpiece, as by contact between the surface 20 of the electrode 18 and a patient's skin, toward a proximal position in which the gap is closed and the end face 111 of the electrode shank urges against the face portion 124 of the second electrical coupler 123. When the gap is closed, as shown in FIGS. 5 and 6, and the end face 111 urges against the face portion 124, the end portion 110 of the electrode can electrically couple to the energizable element 115, placing the handpiece in an activatable configuration.

A resiliently compressible spring element can urge the first electrical coupler 125 and the second electrical coupler 123 away from each other. For example, the spring element can urge the second electrical coupler 123 toward a distal end of the handpiece. Such a spring element can permit the end portion 110 of the shank to move longitudinally in a proximal direction by a distance, x, as shown in FIG. 5. The distance, x, can correspond to a longitudinal component of the force applied between the treatment surface 20 of the electrode and the treatment site, and inversely correspond to a "spring constant" of the spring element. As the electrode 18 urges more forcefully against the treatment site, the electrode and the end portion 110 can move farther in a proximal direction in the handpiece 10 until the second electrical coupler 123 reaches an upper threshold displacement, $x_{max}$, as shown in FIG. 6.

In some instances, the electrically conductive element 120 can comprise an electrically conductive, resiliently compressible spring element 121, as shown in FIG. 4. In other instances, the electrically conductive element 120 can be a separate component from the resiliently compressible spring element. When the second electrical coupler 123 is displaced from the at-rest position shown in FIG. 4, as in FIGS. 5 and 6, a biasing force of the spring (e.g., spring 121) can urge the second electrical coupler 123 toward the distal, at-rest position shown in FIG. 4.

When in an activatable configuration as shown in FIGS. 5 and 6, the spring element 24 can urge against the electrode in a distal direction. As well, the second electrical coupler 123 can urge against the electrode shank in a distal direction under the force of, for example, the resiliently compressible spring element 121.

As the electrode 18 urges less forcefully against the treatment site, the biasing forces of the spring element 24 and, for example, the spring element 121, can urge the electrode and the corresponding end portion 110 distally in the handpiece 10 until the second electrical coupler 123 returns to the at-rest configuration shown in FIG. 4 (e.g., until the gap 117 closes). For example, the energizable element 115 can have a stop member 116 or other limiter configured to limit an extent of distal movement of the second electrical coupler 123.

As but one example of such a limiter, the stop member 116 can be configured as an inwardly extending shoulder, as shown in FIGS. 4, 5 and 6. With such a limiter, the second electrical coupler 123 can return to its at-rest configuration and urge against the stop member 116 or other limiter. When the second electrical coupler is in its at-rest configuration, the spring element 24 can be the only element applying a biasing force in a distal direction to the electrode. The spring element 24 can further urge the electrode toward its at-rest configuration (e.g., toward a position to electrically decouple the electrode from the power element 115) before the patient contact surface 20 of the electrode 18 lifts from a treatment site in or on a patient.

Other embodiments of limiters are possible. For example, one or more guide shafts (not shown) can extend longitudinally through the electrical coupler 123. A distal end of the one or more guide shafts can have a relatively larger dimension (e.g., a relatively larger diameter) as compared to a proximal portion of the respective shaft over which the electrical coupler can translate. The electrical coupler 123 can urge against the larger portion of the shaft at a distal-most position (e.g., in an at-rest configuration), preventing further distal translation of the electrical coupler 123. By preventing further distal movement of the second electrical conductor 123, the energizable electrode 18 can continue to urge distally within the handpiece and open a gap sufficient to electrically decouple the energizable electrode from the energizable element 18.

As noted above, FIG. 8 shows an electrode 218 slidably engaged with a movable shank 216. For example, the electrode 218 and shank 216 assembly shown in FIG. 8 is movable relative to the housing 12 and the immovable power element 30, and the electrode 218 and shank 216 are movable relative to each other. With such an arrangement, a portion of the external surface 216b of the shank 216 and a corresponding portion of the internal surface of the bore 219 are slidingly arranged in relation to each other. Such overlapping regions provide sufficient contact area for electrical current to pass from the shank 216 into the electrode 218. Accordingly, the electrosurgical device shown in FIGS. 8 through 11 is configured to permit the energizable electrode 218 to move while maintaining an electrical coupling between an energized or energizable power element 30 and the energizable electrode 218. Optionally, an electrically conductive lubricant can be applied to the overlapping regions of the bore 219 and shank 216.

In the at-rest configuration shown in FIG. 8, a gap between the end face 26 of the movable shank 216 and the face portion 27 of the power element 30 is sufficiently large as to insulate the end face 26 from the face portion 27, electrically decoupling the end portion of the shank 216 from the energizable element 30. For example, the gap can be sized so as to prevent arcing through the air (or other dielectric material) between the end face 26 and the face portion 27 under a normal operating voltage potential applied across the gap.

Figure 9:
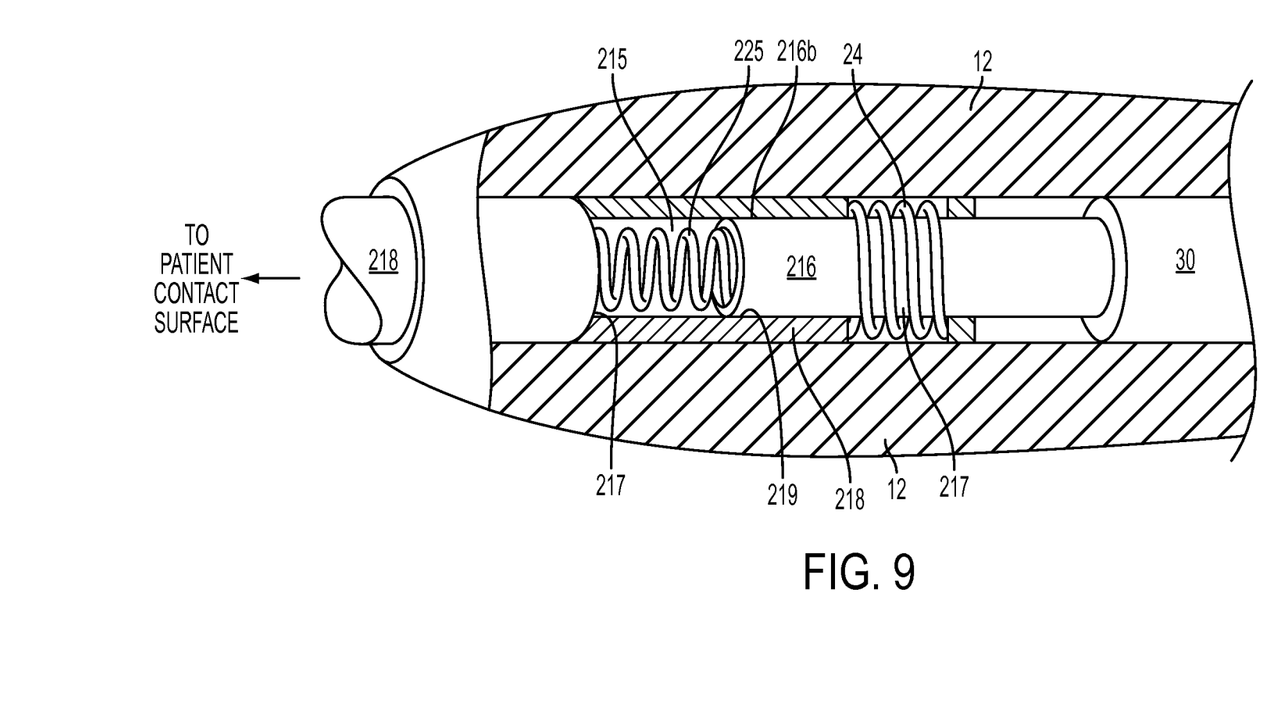
FIG. 9 illustrates an isometric, partially sectioned view of the portion of the device shown in FIG. 8, in an in-use arrangement.

As with the electrode 18 and shank 16 assembly shown in FIGS. 2 and 3, the electrode 218 and shank 216 assembly shown in FIG. 8 can be urged proximally toward the power element 30, as by contact between the surface 20 of the electrode 218 and a patient's skin. For example, the electrode 218 and shank 216 assembly can move toward a proximal position (relative to the handpiece 12) in which the gap between the proximal end face 26 of the shank 216 and the distal end face 27 of the power element 30 is closed, as shown in FIG. 9. When the gap is closed, the circuit-contact surface 26 of the shank 216 can urge against the electrode contact surface 27 of the power element 30, electrically coupling the shank 216 and the power element 30 to each other and placing the handpiece in an activatable configuration. Upon releasing or easing a proximally directed longitudinal force applied to the electrode 218 (e.g., as a user releases or eases pressure exerted on a patient's skin), the electrode 218 and shank 216 assembly can return to the at-rest position shown in FIG. 8 under the biasing force of the externally positioned, resiliently compressible spring 24, as described above.

The illustrated electrode 218 and the shank 216 are also movable relative to each other. As shown in FIGS. 8, 9, 10 and 11, the electrode 218 and the shank 216 can be slidably engaged with each other, allowing the electrode 218 to move relative to the handpiece 12 while remaining energized. More particularly, in an illustrated arrangement, the electrode 218 defines a recessed bore 219 having a recessed end-wall 217 and defining an open region 215 positioned between the end-wall 217 and a distal end 216a of the movable shank 216. The illustrated electrode 218 and shank 216 assembly includes a resiliently compressible bias member 225 (e.g., a coil spring, a leaf spring, etc.) positioned in the open region 215 within the recessed bore 219 to urge the electrode 218 and the shank 216 longitudinally apart from each other.

Figure 11:
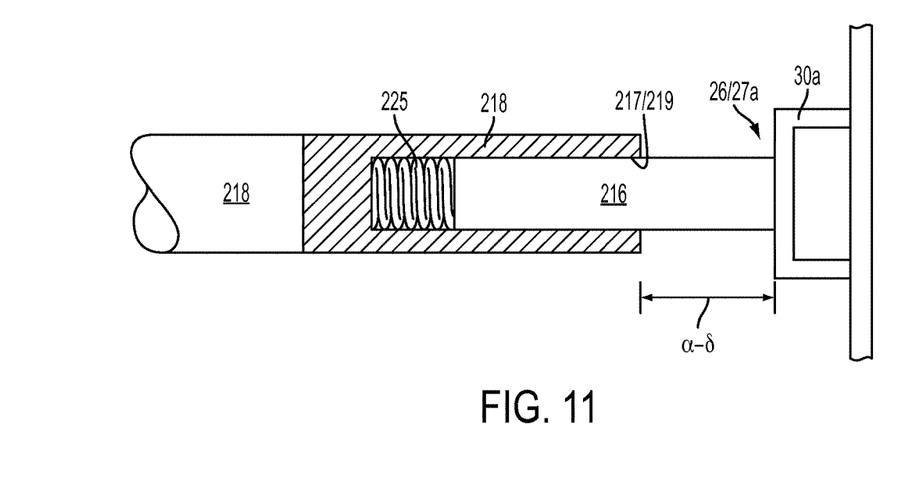
FIG. 11 illustrates a side-elevation view of the device shown in FIG. 10 in an in-use arrangement, as disclosed herein.

With such an arrangement, the electrode 218 and shank 216 assembly can be urged toward the power element 30 until the shank 216 urges or seats against the power element 30. As the shank 216 contacts the power element 30, the shank 216 stops moving proximally into the handpiece relative to the power element 30. However, the longitudinally slidable engagement between the electrode 218 and the shank 216 permit the electrode 218 to continue to move proximally into the handpiece toward the power element 30 and the seated shank 216. Such sliding can continue under pressure applied between the electrode surface 20 and the patient's skin until the bias member 225 in the open region 215 is fully compressed (e.g., as shown in FIGS. 9 and 11).

As FIG. 9 depicts, such relative motion between the electrode 218 and the shank 216 can compress the resiliently compressible bias member 225 in the open region 215. As pressure applied between the electrode surface 20 and the patient's skin decreases, the end-wall 217 of the electrode can urge away from the end-face 216a of the shank 216 under an outwardly directed biasing force applied to the shank 216 and the electrode 218 by the resiliently compressible bias member 225.

In some embodiments, a spring stiffness (or spring coefficient) of the bias member 225 can be selected such that the member 225 expands outwardly with sufficient longitudinal force to overcome an opposing frictional force between the inner wall of the bore 219 and the outer wall of the shank 216. With a spring stiffness as just described, as a user lifts the handpiece 12 away a modest distance from a treatment site while during a therapeutic treatment (e.g., while applying RF energy), the electrode 218 can remain in contact with the treatment site and can remain energized, as the bias member 225 can continue to urge the shank 216 outwardly of the bore 219 and into electrical contact with the power element 30.

Figure 10:
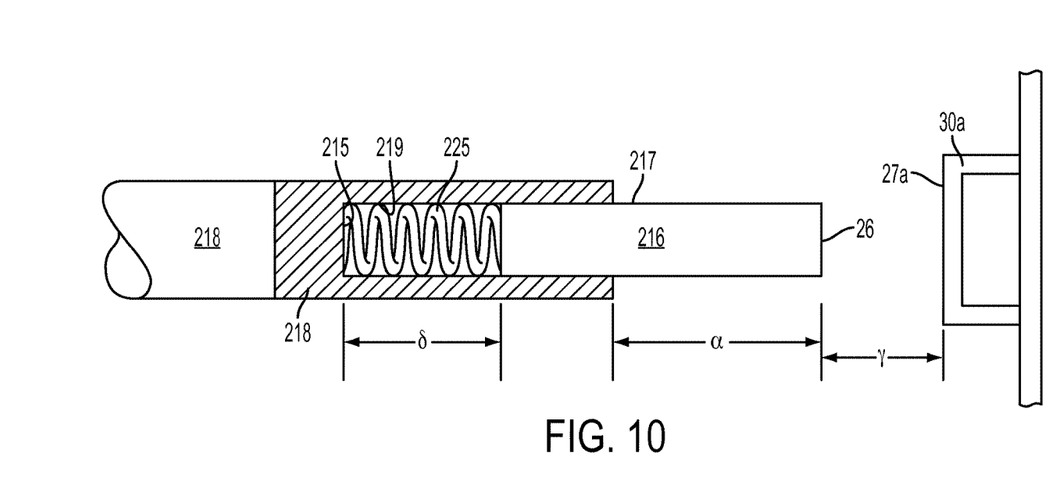
FIG. 10 illustrates a side-elevation view of a partially sectioned electrosurgical device in an at-rest position.

As indicated in FIG. 10, the biasing member 24 can urge the electrode 218 and shank 216 assembly longitudinally away from the power element 30 (e.g., power element 30a) to define a gap between a contact surface 27a and a face 26 of the shank 216. The gap can span a distance $\gamma$ when the electrode and shank are in an at-rest position as shown in FIG. 10. The gap dimension $\gamma$ in the at-rest position can be sufficiently large that the power element 30, 30a is electrically isolated from the shank 216. In the at-rest position, a portion of the shank 216 can extend outwardly of the bore 219 by a distance $\alpha$, and the open region 215 occupied by the bias member 225 can span a compressible distance $\delta$.

When the gap between the power element 30, 30a and the end face 26 of the shank 216 shrinks to or below a given threshold, the power element and the shank 216 can become electrically coupled. When the shank 216 contacts the power element 30, 30a, the gap is closed and the proximal end of the electrode 218 can be spaced by a distance $\alpha$ from the face 27, 27a of the power element 30, 30a. As the electrode 218 is further urged proximally into the handpiece 12, the bias member 225 compresses further, up to a maximum compression distance $\delta$. When the bias member 225 is fully compressed, the proximal end of the electrode 218 can be spaced from the power element by a distance $\alpha-\delta$.

As shown, the electrode 218 defines an axially extending longitudinal bore 219 into which the shank 216 is received as a plunger element in FIGS. 8 through 11. In other embodiments (not shown), the shank 216 defines a longitudinal bore into which the electrode is received as a plunger element. Such an embodiment can include a bias member 225 positioned within the longitudinal bore in the shank. In such an embodiment, a spring 24 can urge against a portion of the shank, and the relative stiffness of the spring 24 and the bias member can be selected such that the electrode 218 remains substantially fixed relative to the shank 216 until the shank seats against the power element.

Other Exemplary Embodiments

Other handpiece configurations are possible. For example, an energizable element 115a can include a dampener 121b in combination with a resiliently compressible spring element 121a. Such a dampener can reduce a rate at which the end portion 110a can move in a proximal direction and a rate at which the energizable element 115a can return to the at-rest configuration.

This disclosure references the accompanying drawings, which form a part hereof, wherein like numerals designate like parts throughout. The drawings illustrate specific embodiments, but other embodiments may be formed and structural and logical changes may be made without departing from the intended scope of this disclosure.

Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" or "or", as well as "and" and "or."

Incorporating the principles disclosed herein, it is possible to provide a wide variety of systems configured to render an electrosurgical handpiece inoperable at or near an end of the handpiece's safe useful life, in addition to the systems described above.

The technologies from any example can be combined with the technologies described in any one or more of the other examples. Accordingly, this detailed description shall not be construed in a limiting sense, and following a review of this disclosure, those of ordinary skill in the art will appreciate the wide variety of electrosurgical systems that can be devised using the various concepts described herein. Moreover, those of ordinary skill in the art will appreciate that the exemplary embodiments disclosed herein can be adapted to various configurations without departing from the disclosed principles. Thus, in view of the many possible embodiments to which the disclosed principles can be applied, it should be recognized that the above-described embodiments are only examples and should not be taken as limiting in scope. We therefore reserve all rights to the subject matter disclosed herein, including the right to claim all that comes within the scope and spirit of the following claims, as well as all combinations of each aspect of all innovations shown or described herein.

The invention claimed is:

1. An electrosurgical device comprising:
    a housing and an electrode defining an energizable surface at least partially positioned externally of the housing and a portion positioned at least partially within the housing;
    a shank portion positioned internally of the housing in a sliding engagement with the housing, wherein the energizable surface and the shank portion are electrically coupled with each other;
    an energizable element positioned in the housing and electrically coupled with the energizable surface and configured to be electrically coupleable with an electrosurgical control unit to energize the energizable surface with therapeutic energy, wherein the electrode and the shank are longitudinally movable relative to the housing and the energizable element in correspondence with each other, wherein the electrode is movable relative to the housing in correspondence with the energizable element when the shank urges against the energizable element;
    a resiliently compressible bias member configured to absorb movement of the energizable element when the shank and the energizable element urge against each other; and
    a spring member so arranged in the housing as to urge the electrode and the shank assembly longitudinally away from the energizable element positioned in the housing.

2. An electrosurgical device according to claim 1, wherein the portion of the electrode positioned at least partially within the housing defines a recessed bore slidably receiving a portion of the shank.

3. An electrosurgical device according to claim 1, wherein the shank defines a recessed bore slidably receiving a portion of the electrode.

4. An electrosurgical device according to claim 1, wherein the electrode is longitudinally movable from an at-rest position to a use position, wherein, when the electrode is positioned in an at-rest position, the shank portion of the electrode and the energizable element are so spaced apart from each other as to define a gap therebetween of sufficient distance to prevent an electrical arc from spanning the gap.

5. An electrosurgical device according to claim 4, wherein the spring member is configured to urge the electrode and the shank assembly distally apart from the energizable element.

6. An electrosurgical device, comprising:
    a housing and an electrode defining an energizable surface at least partially positioned externally of the housing and a shank portion positioned internally of the housing, wherein the energizable surface and the shank portion are electrically coupled with each other;
    an energizable element positioned in the housing and electrically coupled with the energizable surface and configured to be electrically coupleable with an electrosurgical control unit to energize the energizable surface with therapeutic energy and having a first electrical coupler being immovable relative to the housing and a second electrical coupler being movable relative to the housing, wherein the first electrical coupler and the second electrical coupler are electrically coupled to each other, wherein the electrode is movable relative to the housing such that the shank portion is configured to urge against and electrically couple to the second electrical coupler in correspondence with a force applied to the energizable surface of the electrode;
    a first resiliently compressible spring element configured to urge the first electrical coupler and the second electrical coupler apart, and to electrically couple the first electrical coupler to the second electrical coupler;
    a stop member configured to limit an extent of distal movement of the second electrical coupler; and
    a second resiliently compressible spring element configured to urge the electrode distally of the energizable element so as to define a gap between the shank portion of the electrode and the second electrical coupler sufficient to decouple the shank portion of the electrode from the second electrical coupler.

* * * * *